United States Patent
Kim et al.

(10) Patent No.: US 7,867,391 B2
(45) Date of Patent: *Jan. 11, 2011

(54) CUCURBITURIL DERIVATIVE-BONDED SOLID SUBSTRATE AND BIOCHIP USING THE SAME

(75) Inventors: Kimoon Kim, Pohang (KR); Jin Koo Kang, Pohang (KR); Woo Seong Jeon, Pohang (KR); Sang Yong Jon, Pohang (KR); Selvapalam Narayanan, Pohang (KR); Dong Hyun Oh, Pohang (KR); Kangkyun Baek, Pohang (KR)

(73) Assignee: Postech Foundation, Pohang, Kyungsangbuk-do (KR)

( * ) Notice: Subject to any disclaimer, the term of this patent is extended or adjusted under 35 U.S.C. 154(b) by 387 days.

This patent is subject to a terminal disclaimer.

(21) Appl. No.: 10/563,463

(22) PCT Filed: Jul. 5, 2004

(86) PCT No.: PCT/KR2004/001652

§ 371 (c)(1), (2), (4) Date: Jan. 5, 2006

(87) PCT Pub. No.: WO2005/003391

PCT Pub. Date: Jan. 13, 2005

(65) Prior Publication Data

US 2006/0160207 A1 Jul. 20, 2006

(30) Foreign Application Priority Data

Jul. 5, 2003 (KR) .............. 10-2003-0045523

(51) Int. Cl.
*B01D 15/08* (2006.01)
(52) U.S. Cl. ............... 210/198.2; 210/635; 210/656; 506/33; 506/43
(58) Field of Classification Search ............. None
See application file for complete search history.

(56) References Cited

U.S. PATENT DOCUMENTS

| 7,388,099 B2 * | 6/2008 | Kim et al. ............ 548/305.4 |
| 2004/0147396 A1 * | 7/2004 | Richter et al. ............ 502/401 |
| 2006/0207938 A1 * | 9/2006 | Kim et al. ............ 210/656 |

FOREIGN PATENT DOCUMENTS

| KR | 1020010039662 A | 5/2001 |
| KR | 1020010057696 A | 7/2001 |
| KR | 1020020005085 A | 1/2002 |
| KR | 1020030003901 A | 1/2003 |
| KR | 1020030024426 A | 3/2003 |
| KR | 1020030060053 A | 7/2003 |
| WO | 03/004500 A1 | 1/2003 |
| WO | 2004/072151 A1 | 8/2004 |

OTHER PUBLICATIONS

Jon et al., "Facile Synthesis of Cucurbit[n]unil Derivatives . . . " J. Am. Chem. Soc., 2003, vol. 125, pp. 10186-101867.
Lesaicherre et al., "Intein-Mediated Biotinylation of Proteins . . . " J. Am. Chem. Soc., 2002, vol. 124, pp. 8768-8769.
Paborsky, L.R., et al., "A Nickel Chelate Microtiter Plate Assay for Six Histidine-Containing Proteins", Analytical Biochemistry, 234, 1996, pp. 60-65.
Frey, B.L., et al., Control of the Specific Adsorption of Proteins onto Gold Surfaces with Poly(L-lysine) Monolayers, Anal. Chem. 67, 1995, pp. 4452-4457.
Lesaicherre, M., et al., "Intein-Mediated Biotinylation of Proteins and its Application in a Protein Microarray", JACS Comm., J. Am. Chem. Soc., 124, 2002, pp. 8768-8769.

* cited by examiner

*Primary Examiner*—Christopher Low
*Assistant Examiner*—Christopher M. Gross
(74) *Attorney, Agent, or Firm*—Rothwell, Figg, Ernst & Manbeck pc

(57) ABSTRACT

The present disclosure provides a cucurbituril derivative-bonded solid substrate in which cucurbituril derivatives of Formula 1 are covalently bonded to a modified solid substrate of Formula 2. The cucurbituril derivative provides functional groups which can be used to link biomaterials to the substrate. Protein chips, gene chips, and sensors for biomaterial assays having the cucurbituril derivative-bonded solid substrate are also provided.

6 Claims, 3 Drawing Sheets

US 7,867,391 B2

CUCURBITURIL DERIVATIVE-BONDED SOLID SUBSTRATE AND BIOCHIP USING THE SAME

CROSS-REFERENCE TO RELATED APPLICATIONS

This application is a 35 U.S.C. 371 National Phase Entry Application from PCT/KR2004/001652, filed Jul. 5, 2004, designating the U.S.

BACKGROUND OF THE INVENTION

1. Field of the Invention

The present invention relates to a cucurbituril derivative-bonded solid substrate, and more particularly, to a solid substrate covalently bonded with a cucurbituril derivative which can immobilize a biomaterial by a non-covalent interaction, and its applications.

2. Description of the Related Art

After the human genome sequence was drafted in 2000, gene expression could be understood at mRNA level. Thereafter, developments of personalized medicines or diagnostic reagents based on individual genome information have been anticipated. Therefore, there has arisen a need to rapidly trace the expression levels of a large number of genes. In this regard, there was developed a DNA chip capable of simultaneously performing assays of a thousand to ten thousand genes. However, a gene assay alone cannot provide information about proteins which are not only gene products but also biomaterials essential for biological activity. Therefore, there has been suggested a protein chip, a corresponding concept of a DNA chip, which can perform simultaneous assays of a large number of proteins.

The concept of the protein chip is based on the protein microarrays which contain chemically or biochemically treated surfaces for specific interaction with proteins of interest. A protein chip can be made by using a solid substrate illustrated in FIG. 1 as follows: first, a thin film is formed on a solid substrate 4 using compounds with functional groups 1 for linkages with the solid substrate 4 and another functional groups 3 for linkages with biomaterials such as proteins. Then, biomaterials such as proteins can be immobilized on the solid substrate 4 via chemical or physical interactions between biomaterial and the terminal functional group 3. In FIG. 1, 2 refers to a molecular body.

Hitherto, many researchers have used covalent bonds between the functional groups 3 of Reference Diagram 1 and proteins to immobilize the proteins on a solid substrate. When covalent bonds between the functional groups 3 of Reference Diagram 1 and proteins are formed, the proteins can be immobilized on the surface of a solid substrate.

However, it is well-known that their specificities or activities toward substrates are seriously affected by the immobilization method, because the specificity and activity are strongly related to their specific three-dimensional structures and orientation of their active site. Therefore, the three-dimensional structures of proteins may be damaged when the proteins are covalently bonded to a solid substrate, thereby causing degeneration of the proteins, such as a protein 6 shown in FIG. 2. This is because the function of proteins is dependent on their specific three-dimensional structures formed by chains of amino acids constituting the proteins. To maintain the function of a protein chip, like a protein 7 in FIG. 2, an active site must not be bonded to the linkage layer 5 to preserve the functionality of the active site.

To solve this problem, many methods have been developed for immobilizing proteins to a surface of a solid substrate via non-covalent bonds.

By way of an example, a study about the attachment of proteins to a solid substrate by a coordination bond was reported. Paborsky et al. suggested a coordination linkage between proteins fused with histidine, which is an amino acid known to well bind with Ni, Cu, etc., and a surface of a solid substrate to which Ni is attached by nitrilotriacetic acid (NTA) [Paborsky, L. R.; Dunn, K. E.; Gibbs, C. S.; and Dougherty, J. P., Anal. Biochem. 1996, 234, pp. 60-65].

Frey et al. reported the attachment of an intermediate, such as polylysine, capable of ionically binding with proteins, to a solid substrate, to immobilize the proteins on the solid substrate [Frey, Brian L.; Jordan, Claire E.; Kornguth, Steven; and Corn, Robert M., Anal. Chem. 1995, 67, 4452-4457].

Recently, Tae-Sun Kim et al. reported a hydrogen bond between proteins and a solid substrate having crown ether derivatives, paying attention to a hydrogen bond between ammonium groups abundantly present at non-active sites of proteins and crown ether groups (Korean Patent Application Nos. 10-1999-0061074 and 10-2000-0038491).

However, the bond strength of most non-covalent bonds is much less than that of covalent bonds. Therefore, proteins having non-covalent bonds with a solid substrate may be detached from the solid substrate when contact with chemical materials used in immunoassay. In this regard, many attempts have been made to immobilize proteins on a solid substrate via stronger non-covalent bonds.

Recently, Yao and co-workers reported a solid substrate for a protein chip in which avidin, a type of protein, is immobilized on the solid substrate via a covalent bond [Lesaicherre, M.-L.; Lue, R. Y. P.; Chen, G. Y. J.; Zhu, Q.; and Yao, S. Q. J., Am. Chem. Soc. 2002, 124, 8768]. Avidin is known to bind with four small molecules of biotin by a coupling constant of about $10^{15}$ $M^{-1}$, which is the strongest non-covalent bond among currently known non-covalent bonds [Wilchek, M.; Bayer, E. A. Avidin-Biotin Technology. In Methods in Enzymology 1990, 184]. According to the report by Yao et al., probe proteins are fused with biotin and then are immobilized on a solid substrate treated with avidin. Reportedly, the probe proteins are not detached from the solid substrate even under a very severe environment. However, this method has an economical limitation of avidin being costly, even though there is an advantage in that a coupling constant of avidin-biotin interaction is very large.

Therefore, a cost effective method for immobilizing proteins to a solid substrate using a non-covalent bond with strong interaction is required.

SUMMARY OF THE INVENTION

The present invention provides a cucurbituril derivative-bonded solid substrate in which a cucurbituril derivative is covalently bonded to a modified solid substrate.

The present invention also provides a protein chip using the cucurbituril derivative-bonded solid substrate.

The present invention also provides a gene chip using the cucurbituril derivative-bonded solid substrate.

The present invention also provides a sensor for biomaterial assay using the cucurbituril derivative-bonded solid substrate.

According to an aspect of the present invention, there is provided a cucurbituril derivative-bonded solid substrate in which cucurbituril derivatives of Formula 1 below covalently bonded to a modified solid substrate of Formula 2 below act as functional groups for linkage with biomaterials, like functional group 3 of Reference Diagram 1, via non-covalent interactions between portal carbonyl groups of cucurbituril derivatives and ammonium groups of amino acid in biomaterials:

<Formula 1>

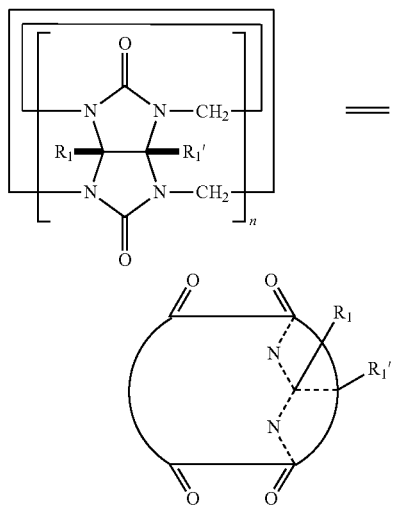

wherein n is an integer of 4 to 20, and $R_1$ and $R_1'$ are each independently an alkenyloxy group with an unsaturated bond end and a substituted or unsubstituted alkyl moiety of $C_1$-$C_{20}$, a carboxyalkylsulfinyloxy group with a substituted or unsubstituted alkyl moiety of $C_1$-$C_{20}$, a carboxyalkyloxy group with a substituted or unsubstituted alkyl moiety of $C_2$-$C_8$, an aminoalkyloxy group with a substituted or unsubstituted alkyl moiety of $C_2$-$C_8$, or a hydroxyalkyloxy group with a substituted or unsubstituted alkyl moiety of $C_2$-$C_8$, and <Formula 2>

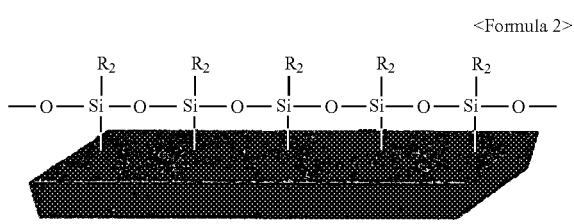

wherein $R_2$ is an alkyl group of $C_1$-$C_{10}$ with an end functional group selected from thiol, amine, epoxy, isocyan, and isothiocyan.

FIG. 1 illustrates a solid substrate 3 covalently bonded with a cucurbituril derivative 1 via a linkage layer 2.

The solid substrate of Formula 2 may be a glass, a silicon wafer, an indium tin oxide (ITO) glass, an aluminum oxide substrate, or a titanium dioxide substrate.

Preferably, the cucurbituril derivative-bonded solid substrate is one selected from substrates represented by Formulae 3 through 6:

<Formula 3>

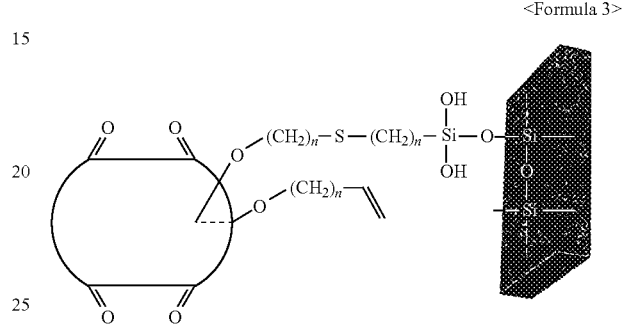

wherein each n is independently an integer of 1 to 20;

<Formula 4>

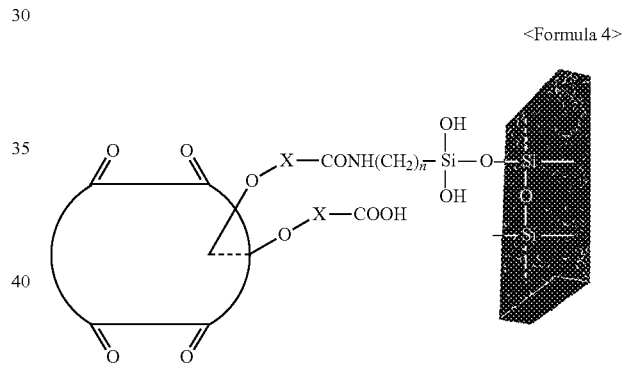

wherein n is an integer of 1 to 20 and X is a dialkylsulfide group with a substituted or unsubstituted alkyl moiety of $C_1$-$C_{20}$ or a substituted or unsubstituted alkyl group of $C_1$-$C_{20}$;

<Formula 5>

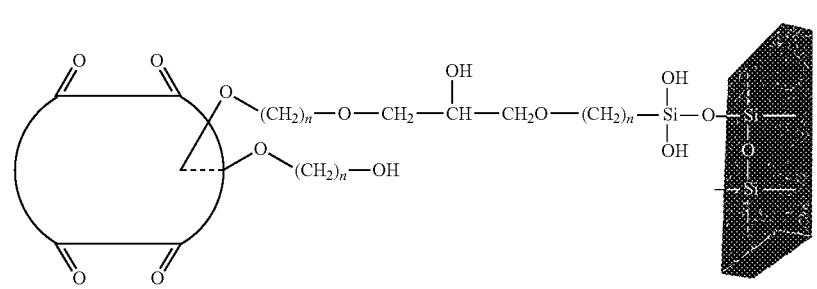

wherein n is an integer of 1 to 20; and

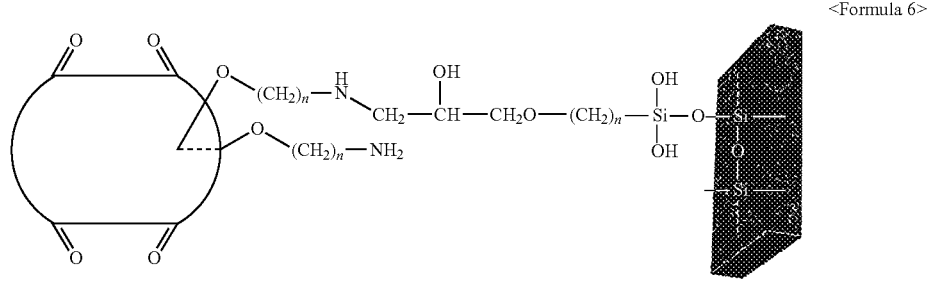

<Formula 6> wherein n is an integer of 1 to 20.

According to another aspect of the present invention, there is provided a cucurbituril derivative-bonded solid substrate in which a cucurbituril derivative of Formula 1 below is covalently bonded to a modified solid substrate of Formula 7 below:

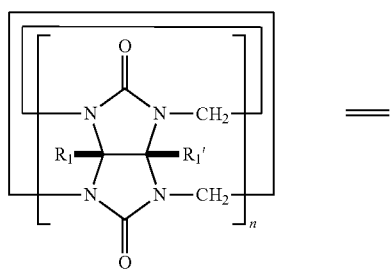

<Formula 1>

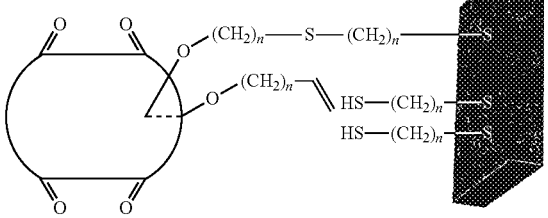

<Formula 8> wherein each n is independently an integer of 1 to 20;

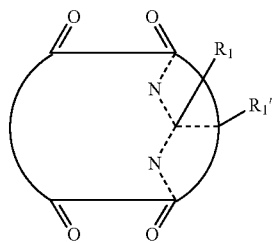

wherein n and $R_1$ are as defined in the above, and

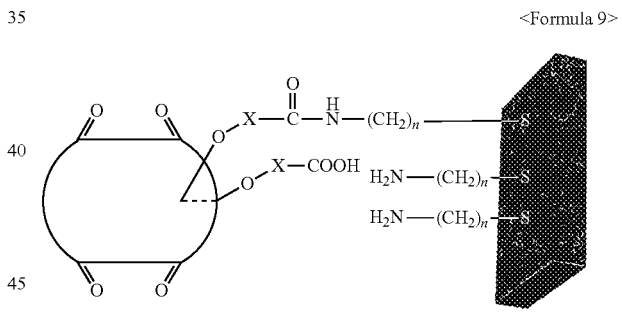

<Formula 9> wherein each n is independently an integer of 1 to 20 and X is a dialkylsulfide group with a substituted or unsubstituted alkyl moiety of $C_1$-$C_{20}$ or a substituted or unsubstituted alkyl group of $C_1$-$C_{20}$;

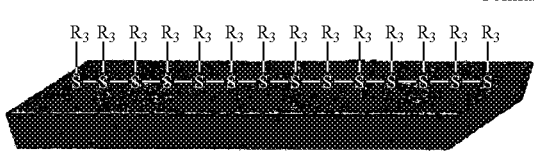

<Formula 7> wherein $R_3$ is an alkyl group of $C_1$-$C_{10}$ with an end functional group selected from thiol, amine, epoxy, isocyan, and isothiocyan.

The solid substrate of Formula 7 may be a substrate made of gold, silver, platinum, or copper.

Preferably, the cucurbituril derivative-bonded solid substrate is one selected from substrates represented by Formulae 8 through 11:

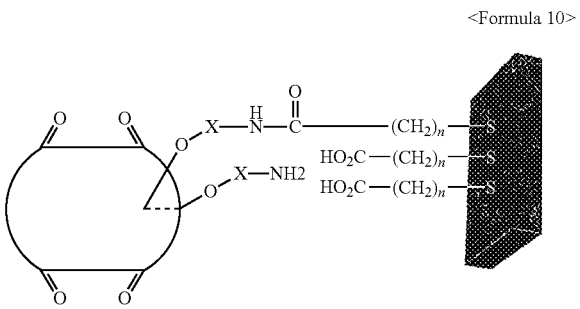

<Formula 10> wherein each n is independently an integer of 1 to 20 and X is a dialkylsulfide group with a substituted or unsubstituted alkyl moiety of $C_1$-$C_{20}$ or a substituted or unsubstituted alkyl group of $C_1$-$C_{20}$; and <Formula 11>

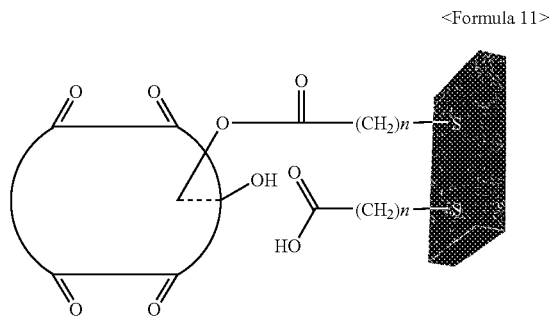

wherein each n is independently an integer of 1 to 20.

According to another aspect of the present invention, there is provided a protein chip including the cucurbituril derivative-bonded solid substrate.

According to another aspect of the present invention, there is provided a gene chip including the cucurbituril derivative-bonded solid substrate.

According to yet another aspect of the present invention, there is provided a sensor for biomaterial assay including the cucurbituril derivative-bonded solid substrate.

Hereinafter, the present invention will be described in detail.

According to the present invention, there is used a cucurbituril derivative represented by Formula 1 below having a functional group suitable for a covalent linkage with a solid substrate:

<Formula 1>

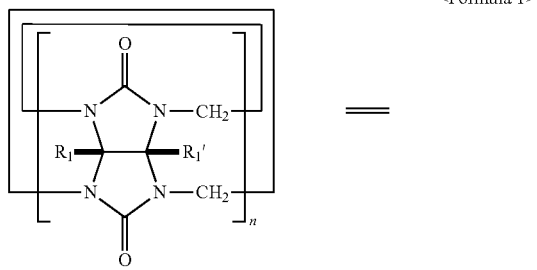

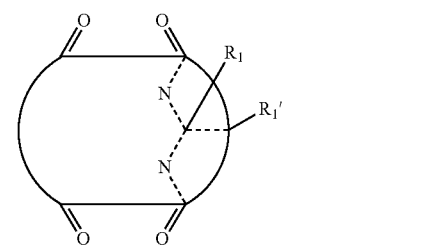

wherein n is an integer of 4 to 20, and $R_1$ and $R_1'$ are each independently an alkenyloxy group with an unsaturated bond end and a substituted or unsubstituted alkyl moiety of $C_1$-$C_{20}$, a carboxyalkylsulfinyloxy group with a substituted or unsubstituted alkyl moiety of $C_1$-$C_{20}$, a carboxyalkyloxy group with a substituted or unsubstituted alkyl moiety of $C_2$-$C_8$, an aminoalkyloxy group with a substituted or unsubstituted alkyl moiety of $C_2$-$C_8$, or a hydroxyalkyloxy group with a substituted or unsubstituted alkyl moiety of $C_2$-$C_8$.

The solid substrate may be a glass, a silicon wafer, an indium tin oxide (ITO) glass, an aluminum oxide substrate, or a titanium dioxide substrate. Examples of hydroxycucurbituril and its mother cucurbituril used as a synthetic material for the compound of Formula 1 above are disclosed together with their structural formulae and synthetic methods in Korean Patent Application Nos. 02-68362, 02-318, 01-57573, 01-39756, and 00-33026, filed by the present applicants, the disclosures of which are incorporated herein by reference in their entireties.

The cucurbituril derivative of Formula 1 is covalently bonded to a modified solid substrate with various end functional groups to form a desired solid substrate. For this, a modified solid substrate of Formula 2 below may be used:

<Formula 2>

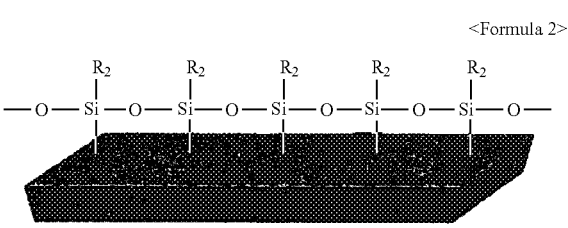

wherein $R_2$ is an alkyl group of $C_1$-$C_{10}$ with an end functional group selected from thiol, amine, epoxy, isocyan, and isothiocyan.

For example, the modified substrate of Formula 2 may be prepared by reacting a silane having an end functional group, such as thiol, amino, and epoxy, with a metal oxide substrate containing a —OH surface group by washing.

A cucurbituril-bonded solid substrate of the present invention can be prepared by covalently bonding the cucurbituril derivative of Formula 1 with the modified solid substrate of Formula 2. That is, the cucurbituril derivative of Formula 1 is covalently bonded to the modified solid substrate of Formula 2 by reacting end functional groups of the cucurbituril derivative, such as a carboxyl group, an amine group, a hydroxyl group, or an allyl group, with end functional groups of the modified solid substrate, such as an amine group, an epoxy group, or a thiol group.

Examples of the solid substrate thus prepared are presented in the following Formulae 3 through 6 and their preparation methods will now be described.

<Formula 3>

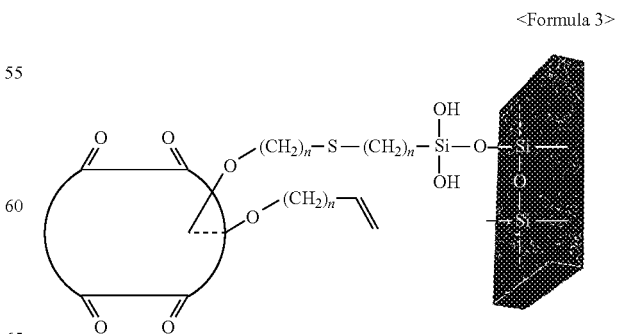

wherein each n is independently an integer of 1 to 20.

A substrate of Formula 3 may be obtained by sulfido-bond formation between a cucurbituril derivative and a solid substrate, in detail, by radical reaction between a thiol-modified metal oxide substrate and alkenyloxycucurbituril.

In more detail, the preparation of the substrate of Formula 3 by radical reaction includes, but is not limited to, the steps of:

(a) dissolving alkenyloxycucurbituril in an organic solvent such as chloroform and methanol;

(b) adding a catalytic amount of AIBN (2,2-azobisisobutyronitrile) to the reaction mixture and then placing the resultant reaction mixture in a crystal tube;

(c) adding a thiol-modified metal oxide substrate to the reaction mixture;

(d) removing residual oxygen by the supply of nitrogen or argon to the reaction mixture;

(e) exposing the reaction mixture to ultraviolet light for several days, for example, 3 days; and (f) washing the resultant solution with excess organic solvent followed by filtration to obtain a metal oxide substrate linked with cucurbituril by a sulfido-bond.

wherein n is an integer of 1 to 20 and X is a dialkylsulfide group with a substituted or unsubstituted alkyl moiety of $C_1$-$C_{20}$ or a substituted or unsubstituted alkyl group of $C_1$-$C_{20}$.

The substrate of Formula 4 may be obtained by amide bond formation between a cucurbituril derivative and a solid substrate, in detail, by amide bond formation between a carboxyl-ended cucurbituril derivative and an amino-modified metal oxide substrate.

In more detail, the preparation of the substrate of Formula 4 includes, but is not limited to, the steps of:

(a) adding 1-ethyl-3-(3-dimethylaminopropyl)carboimidehydrochloride and N-hydroxysuccinimide or N,N-dimethylacetamide to a solution of carboxyl-ended cucurbituril derivative in distilled dimethylformamide;

(b) adding an amino-modified solid substrate to the reaction mixture followed by stirring at room temperature for 12 hours or more;

(c) washing the resultant metal oxide substrate with water and an organic solvent followed by drying to prepare a metal oxide substrate linked with cucurbituril by an amide bond.

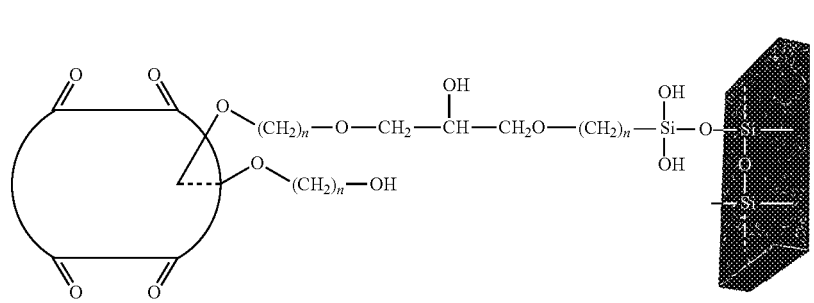

<Formula 5>

The exposure to ultraviolet light in step (e) may be substituted by heating at 80 to 120° C.

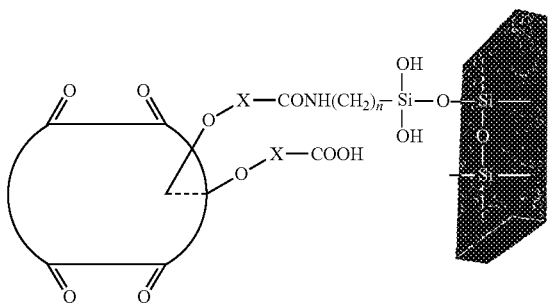

<Formula 4> wherein n is an integer of 1 to 20.

The substrate of Formula 5 may be obtained by ether bond formation between a cucurbituril derivative and a solid substrate, in detail, by a nucleophilic substitution reaction between a hydroxyl-ended cucurbituril derivative and an epoxy-modified metal oxide substrate.

The preparation of the substrate of Formula 5 by nucleophilic substitution reaction includes the steps of:

(a) adding hydroxyalkyloxycucurbituril with an end hydroxyl group to a dimethylformamide solvent;

(b) gradually adding an epoxy-modified metal oxide substrate and a catalytic amount of boron trichloride to the reaction mixture;

(c) stirring the reaction mixture at room temperature for 1 to 24 hours followed by further stirring at 85° C. for 1 to 24 hours; and (d) washing the resultant metal oxide substrate with water and an organic solvent followed by drying to prepare a metal oxide substrate linked with cucurbituril by an ether bond.

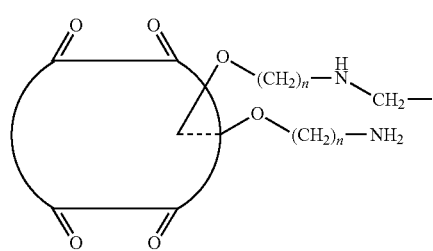 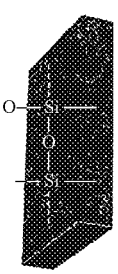

<Formula 6> wherein n is an integer of 1 to 20.

The substrate of Formula 6 may be obtained by amino bond formation between a cucurbituril derivative and a solid substrate, in detail by a nucleophilic substitution reaction between an amino-ended cucurbituril derivative and an epoxy-modified metal oxide substrate.

The preparation of the substrate of Formula 6 by the nucleophilic substitution reaction includes the steps of:

(a) dissolving aminoalkyloxycucurbituril with an end amino group in a phosphate buffer (pH 7 to 10);

(b) adding an epoxy-modified metal oxide substrate to the reaction mixture;

(c) stirring the reaction mixture at room temperature for 1 to 24 hours; and (d) washing the resultant metal oxide substrate with water and an organic solvent followed by drying to prepare a metal oxide substrate linked with cucurbituril by an amino bond.

The present invention also provides a cucurbituril derivative-bonded solid substrate prepared by covalently bonding the cucurbituril derivative of Formula 1 to a solid substrate of Formula 7 below:

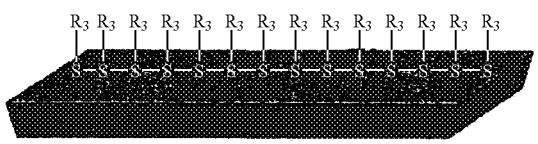

<Formula 7> wherein $R_3$ is an alkyl group of $C_1$-$C_{10}$ with an end functional group selected from thiol, amine, epoxy, isocyan, and isothiocyan.

For example, the modified substrate of Formula 7 may be prepared by reacting a thiol compound having an end functional group, such as thiol, amino, and carboxyl group, with a metal oxide substrate containing a —OH surface group by washing.

A covalent bond between the cucurbituril derivative of Formula 1 and the modified solid substrate of Formula 7 enables the formation of another cucurbituril derivative-bonded solid substrate of the present invention. That is, the cucurbituril derivative of Formula 1 is covalently bonded to the modified solid substrate of Formula 7 by reacting end functional groups of the cucurbituril derivative, such as carboxyl group, an amino group, or a thiol group, with end functional groups of the modified solid substrate, such as an amino group, a carboxyl group, or a thiol group.

Examples of the solid substrate thus prepared are presented in the following Formulae 8 through 11 and their preparation methods will now be described.

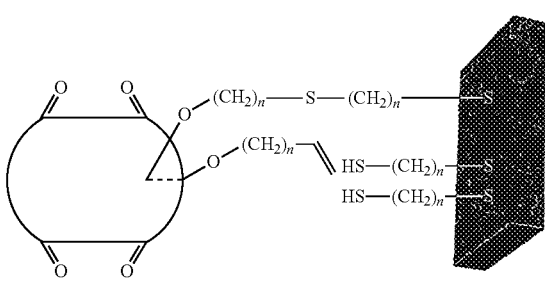

<Formula 8> wherein each n is independently an integer of 1 to 20.

A substrate of Formula 8 may be obtained by sulfide-bond formation between a cucurbituril derivative and a metal substrate, in detail, by radical reaction between a thiol-modified metal substrate and alkenyloxycucurbituril.

In more detail, the preparation of the substrate of Formula 8 by radical reaction includes, but is not limited to, the steps of:

(a) dissolving alkenyloxycucurbituril in an organic solvent such as chloroform and methanol;

(b) adding a catalytic amount of AIBN (2,2-azobisisobutyronitrile) to the reaction mixture and then placing the resultant reaction mixture in a crystal tube;

(c) adding a thiol-modified metal substrate to the reaction mixture;

(d) removing residual oxygen by the supply of nitrogen or argon to the reaction mixture;

(e) exposing the reaction mixture to ultraviolet light for several days, for example, 3 days; and (f) washing the resultant solution with an excess organic solvent followed by filtration to obtain a metal oxide substrate linked with cucurbituril by a sulfide-bond.

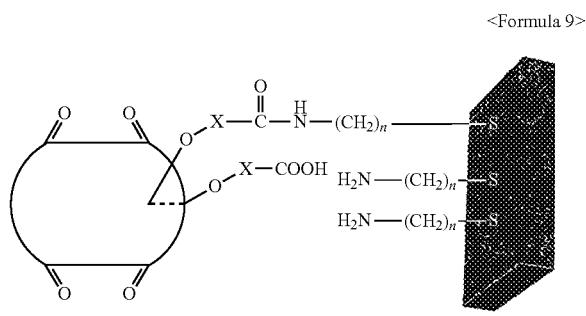

<Formula 9> wherein each n is independently an integer of 1 to 20 and X is a dialkylsulfide group with a substituted or unsubstituted alkyl moiety of $C_1$-$C_{20}$ or a substituted or unsubstituted alkyl group of $C_1$-$C_{20}$.

The substrate of Formula 9 may be obtained by amide bond formation between a cucurbituril derivative and a metal substrate, in detail, by amide bond formation between a carboxyl-ended cucurbituril derivative and an amino-modified metal substrate.

In more detail, the preparation of the substrate of Formula 9 includes, but is not limited to, the steps of:

(a) adding 1-ethyl-3-(3-dimethylaminopropyl)carboimidehydrochloride and N-hydroxysuccinimide or N,N-dimethylacetamide to a solution of carboxyl-ended cucurbituril in distilled dimethylformamide;

(b) adding an amino-modified metal substrate to the reaction mixture followed by stirring at room temperature for 12 hours or more; and (c) washing the resultant metal substrate with water and an organic solvent followed by drying to prepare a metal substrate linked with cucurbituril by an amide bond.

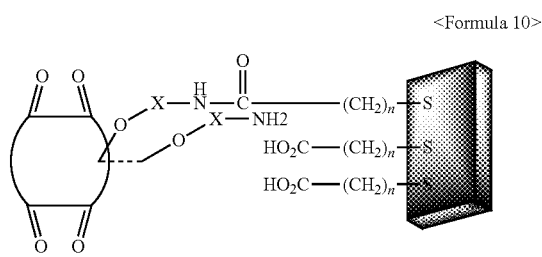

<Formula 10> wherein each n is independently an integer of 1 to 20 and X is a alkylsulfidoalkyl group with a substituted or unsubstituted alkyl moiety of $C_1$-$C_{20}$ or a substituted or unsubstituted alkyl group of $C_1$-$C_{20}$.

The substrate of Formula 10 may be prepared by amide bond formation between a cucurbituril derivative and a metal oxide substrate, in detail, by amide bond formation between a carboxyl-ended cucurbituril derivative and an amino-modified metal oxide substrate.

In more detail, the preparation of the substrate of Formula 10 includes, but is not limited to, the steps of:

(a) dissolving 1-ethyl-3-(3-dimethylaminopropyl)carboimidehydrochloride and N-hydroxysuccinimide or N,N-dimethylacetamide in distilled dimethylformamide and adding a carboxyl-modified metal substrate to the reaction mixture;

(b) adding an amino-ended cucurbituril derivative to the reaction mixture followed by stirring at room temperature for 12 hours or more; and (c) washing the resultant metal substrate with water and an organic solvent followed by drying to prepare a metal substrate linked with cucurbituril by an amide bond.

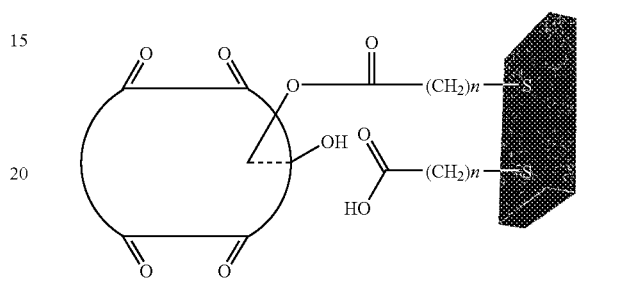

<Formula 11> wherein each n is independently an integer of 1 to 20.

The preparation of the substrate of Formula 11 includes the steps of:

(a) dissolving methylmorpholine and ethylchloroformate to distilled dimethylformamide and adding a carboxyl-modified metal substrate followed by stirring for several minutes;

(b) washing the resultant metal substrate with an organic solvent followed by drying to obtain a metal substrate containing carboxylic anhydride;

(c) dissolving hydroxyl-ended cucurbituril and methylmorpholine to distilled dimethylformamide and adding the resultant metal substrate to the reaction mixture; and (d) washing the resultant metal substrate with water and an organic solvent followed by drying to prepare a metal substrate linked with cucurbituril by an ester bond.

Preferably, a cucurbituril derivative-bonded solid substrate according to the present invention is further subjected to drying and purification after being sufficiently washed with water and an organic solvent to remove residual impurities.

The present invention also provides a protein chip including the cucurbituril derivative-bonded solid substrate. Cucurbituril has carbonyl groups on the entrance of its cavity, and thus, can retain various ionic compounds such as organic cations and high polarity compounds by charge-polarity interactions, polarity-polarity interactions, or hydrogen bonds. In particular, cucurbituril is bonded to diaminoalkane salt by a coupling constant of about $10^6$ $M^{-1}$, which is smaller than that of avidin-biotin interaction but is larger than that of a common non-covalent bond such as a coordination bond or a hydrogen bond. Therefore, a protein chip including the cucurbituril derivative-bonded solid substrate has advantages such as low manufacturing costs, a strong coupling constant, and immobilization of proteins on a solid substrate without damage to active sites of the proteins.

In addition, the cucurbituril derivative-bonded solid substrate of the present invention is covalently bonded to genes or biomaterials, and thus, can be used in preparation of a gene chip and a sensor for biomaterial assay.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Figure 1:
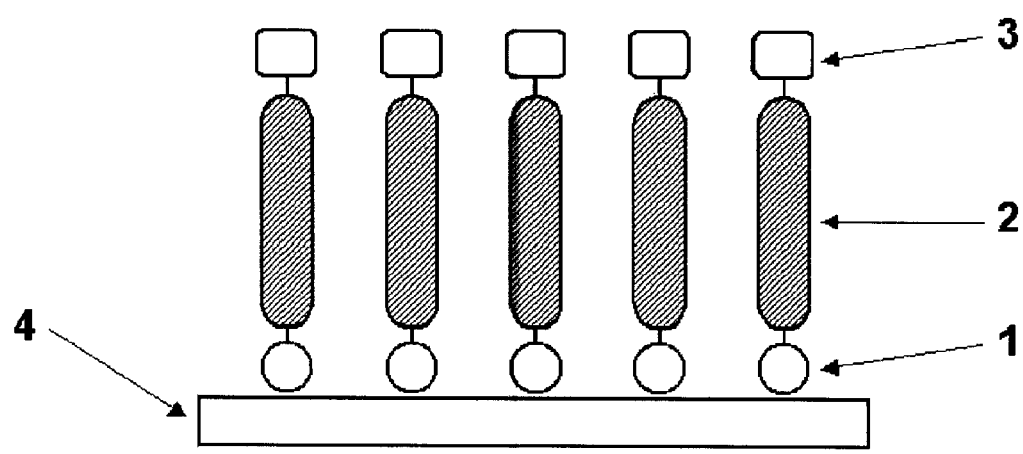
FIG. 1 is a diagram illustrating a solid substrate 4 having a thin film made of compounds with functional groups 1 for linkages with the solid substrate 4 and functional groups 3 for linkages with biomaterials such as proteins.
Figure 2:
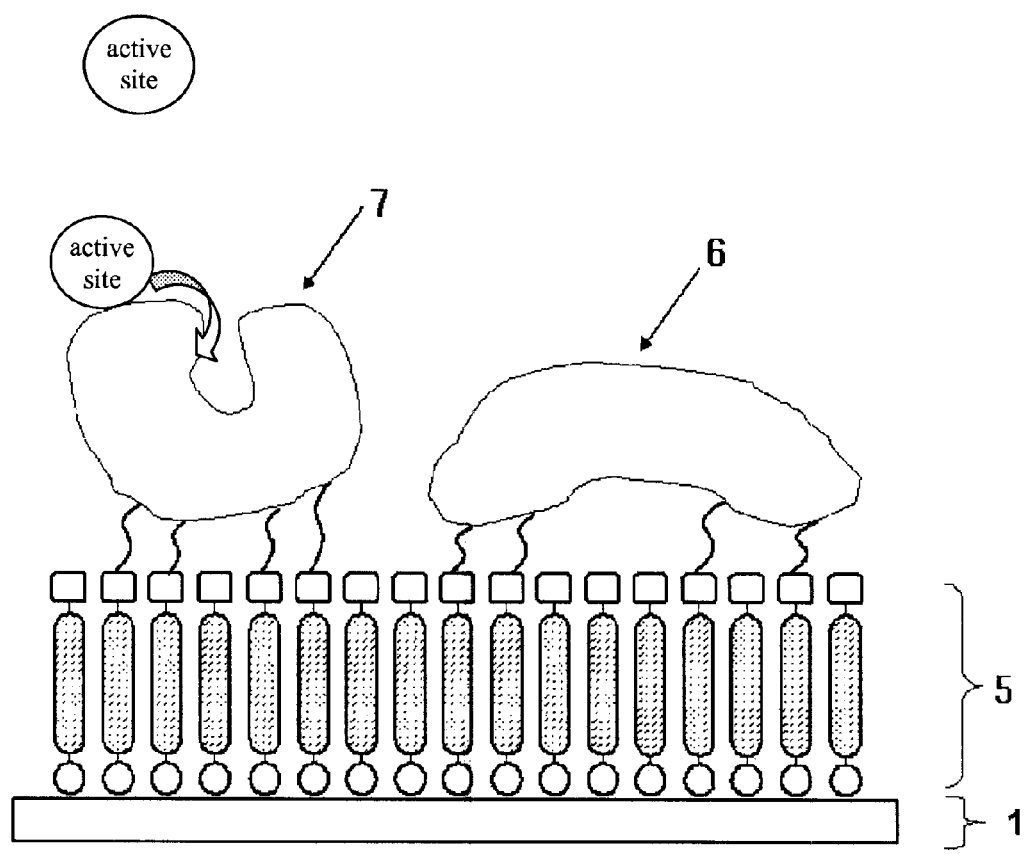
FIG. 2 is a diagram illustrating three-dimensional structures of proteins that are covalently bonded to a solid substrate.
Figure 3:
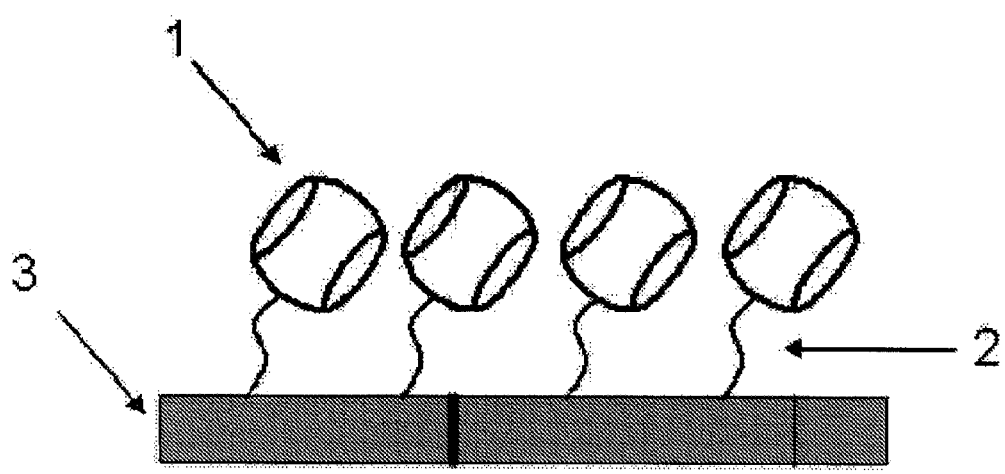
FIG. 3 is a diagram illustrating a cucurbituril derivative-covalent bonded solid substrate.

Hereinafter, the present invention will be described more specifically by Examples. However, the following Examples are provided only for illustrations and thus the present invention is not limited to or by them.

EXAMPLE 1

Preparation of Cucurbituril Derivative-bonded Solid Substrate

A glass substrate was washed with a piranha solution (a 3:1 mixture of sulfuric acid and hydrogen peroxide) to introduce a hydroxyl group to a surface of the glass substrate, sufficiently dried under a reduced pressure, and added in a 20 ml vial under a nitrogen atmosphere. Then, a 10 mM solution of (3-mercaptopropyl)triethoxysilane in toluene was added thereto and incubated at room temperature to perform silanization. After the silanization was completed, the glass substrate was washed with toluene and heated at 120° C. under a reduced pressure for one hour. The glass substrate was placed in a crystal tube, and a solution of 10 mg allyloxycucurbit[6]uril of Formula 1 where $R_1$ is an allyloxy group in a 1:1 mixed solvent of chloroform and methanol was added thereto. The reaction mixture underwent oxygen removal by the supply of nitrogen in the crystal tube and then exposed to ultraviolet light with a wavelength of 300 nm for 36 hours. After the reaction terminated, the resultant glass substrate was sequentially washed with dimethylsulfoxide, dimethylformamide, chloroform, methanol, and acetone, and dried under a reduced pressure.

EXAMPLE 2

Preparation of Cucurbituril Derivative-bonded Solid Substrate

A glass substrate was washed with a piranha solution to introduce a hydroxyl group to a surface of the glass substrate, sufficiently dried under a reduced pressure, and added in a 20 ml vial under a nitrogen atmosphere. Then, a 10 mM solution of (3-aminopropyl)triethoxysilane in toluene was added thereto and incubated at room temperature to perform silanization. After the silanization was completed, the glass substrate was washed with toluene and heated at 120° C. under a reduced pressure for one hour. 10 mg of carboxymethyl-sulfinylpropyloxycucurbit[6]uril of Formula 1 where $R_1$ is a carboxymethylsulfinylpropyloxy group was dissolved in 10 mL of dimethylformamide, and 150 mg of 1-ethyl-3-(3-dimethylaminopropyl)carbodiimide hydrochloride (EDAC) and 3 mg of N-hydroxysuccinimide were then added thereto. The amino-modified glass substrate was placed in the resultant solution and stirred at room temperature for 12 hours. After the reaction terminated, the resultant glass substrate was sequentially washed with dimethylformamide, methanol, water, and acetone, and dried under a reduced pressure.

EXAMPLE 3

Preparation of Cucurbituril Derivative-bonded Solid Substrate

A glass substrate was washed with a piranha solution to introduce a hydroxyl group to a surface of the glass substrate, sufficiently dried under a reduced pressure, and added in a 20 ml vial under a nitrogen atmosphere. Then, a 10 mM solution of (3-aminopropyl)triethoxysilane in toluene was added thereto and incubated at room temperature to perform silanization. After the silanization was completed, the glass substrate was washed with toluene and heated at 120° C. under a reduced pressure for one hour. The resultant amino-modified glass substrate was immersed in a solution of 100 mg of succinic anhydride in diemethylformamide and stirred at room temperature for 12 hours. After the reaction terminated, the glass substrate was sequentially washed with dimethylformamide, water, methanol, and acetone, and dried under a reduced pressure. 10 mg of aminocucurbit[6]uril of Formula 1 where $R_1$ is an amino group was dissolved in 10 mL of dimethylformamide, and 150 mg of EDAC and 3 mg of N-hydroxysuccinimide were then added thereto. Then, the glass substrate was placed in the resultant solution and stirred at room temperature for 12 hours. After the reaction terminated, the resultant glass substrate was sequentially washed with dimethylformamide, methanol, water, and acetone, and dried under a reduced pressure.

EXAMPLE 4

Preparation of Cucurbituril Derivative-bonded Solid Substrate

A glass substrate was washed with a piranha solution to introduce a hydroxyl group to a surface of the glass substrate, sufficiently dried under a reduced pressure, and added in a 20 ml vial under a nitrogen atmosphere. Then, a 10 mM solution of (3-glycidoxypropyl)triethoxysilane in toluene was added thereto and incubated at room temperature to perform silanization. After the silanization was completed, the glass substrate was washed with toluene and heated at 120° C. under a reduced pressure for one hour. 10 mg of 2-hydroxyethyloxycucurbit[6]uril of Formula 1 where $R_1$ is a 2-hydroxyethyloxy group and the resultant glycidoxy-modified glass substrate were placed in 10 mL of dimethylformamide. Then, a catalytic amount of boron trifluoride ($BF_3$) and diethylether ($Et_2O$) were added thereto and stirred at room temperature for two hours, followed by further stirring at 85° C. for 12 hours. After the reaction terminated, the resultant glass substrate was sequentially washed with dimethylformamide, chloroform, methanol, water, and acetone, and dried under a reduced pressure.

EXAMPLE 5

Preparation of Cucurbituril Derivative-bonded Solid Substrate

A glass substrate was washed with a piranha solution to introduce a hydroxyl group to a surface of the glass substrate, sufficiently dried under a reduced pressure, and added in a 20 ml vial under a nitrogen atmosphere. Then, a 10 mM solution of (3-glycidoxypropyl)triethoxysilane in toluene was added thereto and incubated at room temperature to perform silanization. After the silanization was completed, the glass substrate was washed with toluene and heated at 120° C. under a reduced pressure for one hour. 10 mg of 2-aminoethyloxycucurbit[6]uril of Formula 1 where $R_1$ is a 2-aminoethyloxy group and the resultant glycidoxy-modified glass substrate were placed in a phosphate buffer (pH 8.8) and stirred for 12 hours. After the reaction terminated, the resultant glass substrate was immersed in 10 mL of 0.2N HCl solution, stirred for 30 minutes, sequentially washed with water, acetone, and methanol, and dried under a reduced pressure.

EXAMPLE 6

Preparation of Cucurbituril Derivative-bonded Solid Substrate

A gold-deposited silicon wafer was washed with a piranha solution, sufficiently dried under a reduced pressure, and added in a 20 ml vial under a nitrogen atmosphere. Then, a 1 mM solution of 1,8-octanedithiol in ethanol was added thereto and incubated at room temperature to obtain a thiol-modified gold substrate. The thiol-modified gold substrate (in Formula 2, $R_2$ is a propylthiol group) was placed in a test tube and a solution of allyloxycucurbit[6]uril of Formula 1 where $R_1$ is an allyloxy group in 5 mL of a 1:1 mixed solvent of chloroform and methanol was added thereto. The reaction mixture underwent oxygen removal by the supply of nitrogen in the test tube and then exposed to ultraviolet light with a wavelength of 300 nm for 36 hours. After the reaction terminated, the resultant gold substrate was sequentially washed with dimethylsulfoxide, dimethylformamide, chloroform, methanol, and acetone, and dried under a reduced pressure.

EXAMPLE 7

Preparation of Cucurbituril Derivative-bonded Solid Substrate

A gold-deposited silicon wafer was washed with a piranha solution, sufficiently dried under a reduced pressure, and added in a 20 ml vial under a nitrogen atmosphere. Then, a 1 mM solution of 2-aminoethanediol in ethanol was added thereto and incubated at room temperature to obtain an amino-modified gold substrate. 10 mg of carboxymethylsulfinylpropyloxycucurbit[6]uril of Formula 1 wherein $R_1$ is a carboxymethylsulfinylpropyloxy group was dissolved in 10 mL of dimethylformamide, and 150 mg of EDAC and 3 mg of N-hydroxysuccinimide were added thereto. The amino-modified gold substrate was added to the resultant solution and stirred at room temperature for 12 hours. After the reaction terminated, the gold substrate was sequentially washed with dimethylformamide, methanol, water, and acetone, and dried under a reduced pressure.

EXAMPLE 8

Preparation of Cucurbituril Derivative-bonded Solid Substrate

A gold-deposited silicon wafer was washed with a piranha solution, sufficiently dried under a reduced pressure, and added in a 20 ml vial under a nitrogen atmosphere. Then, a 1 mM solution of 11-mercaptoundecanoic acid in ethanol was added thereto and incubated at room temperature to obtain a carboxyl-modified gold substrate. The carboxyl-modified gold substrate was immersed in a solution of 100 mg of succinic anhydride in dimethylformamide and stirred at room temperature for 12 hours. 10 mg of aminocucurbit[6]uril of Formula 1 wherein $R_1$ is an amino group was dissolved in 10 mL of dimethylformamide, and 150 mg of EDAC and 3 mg of N-hydroxysuccinimide were added thereto. The carboxyl-modified gold substrate was added to the resultant solution and stirred at room temperature for 12 hours. After the reaction terminated, the resultant gold substrate was sequentially washed with dimethylformamide, methanol, water, and acetone, and dried under a reduced pressure.

EXAMPLE 9

Preparation of Cucurbituril Derivative-bonded Solid Substrate

A gold-deposited silicon wafer was washed with a piranha solution, sufficiently dried under a reduced pressure, and added in a 20 ml vial under a nitrogen atmosphere. Then, a 1 mM solution of 11-mercaptoundecanoic acid in ethanol was added thereto and incubated at room temperature to obtain a carboxyl-modified gold substrate. The gold substrate was immersed in 10 mL of anhydrous diemethylformamide under a nitrogen atmosphere, and 100 µl of N-methylmorpholine and 100 µl of ethylchloroformate were sequentially added thereto, followed by stirring for 24 hours. After the reaction terminated, the gold substrate was several times washed with diethylether and dried under a reduced pressure. 10 mL of anhydrous dimethylformamide was added to the gold substrate and 10 mL of 2-hydroxyethyloxycucurbit[6]uril of Formula 1 wherein $R_1$ is a 2-hydroxyethyloxy group under a nitrogen atmosphere and stirred for 24 hours. After the reaction terminated, the gold substrate was sequentially washed with dimethylformamide, water, methanol, and acetone, and dried under a reduced pressure.

While the above Examples has been particularly shown and described in terms of only specific bonds between cucurbituril and a solid substrate, it will be understood by those of ordinary skill in the art that synthesis of a solid substrate linked with cucurbituril is possible by various types of bonds.

As apparent from the above description, a cucurbituril derivative-bonded solid substrate according to the present invention enables immobilization of proteins on a surface of the solid substrate via a non-covalent bond with a very strong coupling constant. Based on this property of the solid substrate, a protein chip with no damage to active sites of proteins can be prepared in a cost-effective manner.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cucurbituril derivative-bonded solid substrate in which a cucurbituril derivative of Formula 1 below is covalently bonded to a modified solid substrate of Formula 2 below:

(1)

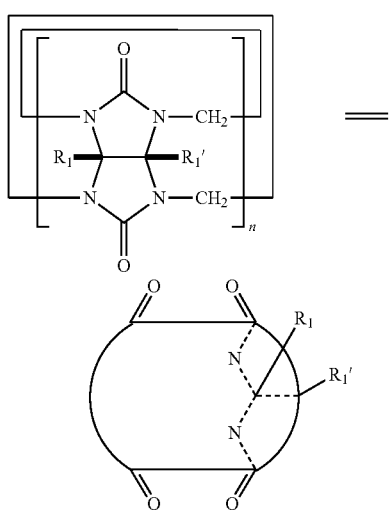

wherein n is an integer of 4 to 20, and R1 and R1' are each independently an alkenyloxy group with an unsaturated bond end and a substituted or unsubstituted alkyl moiety of $C_1$-$C_{20}$, a carboxyalkylsulfinyloxy group with a substituted or unsubstituted alkyl moiety of $C_1$-$C_{20}$, a carboxyalkyloxy group with a substituted or unsubstituted alkyl moiety of $C_2$-$C_8$, an aminoalkyloxy group with a substituted or unsubstituted alkyl moiety of $C_2$-$C_8$, or a hydroxyalkyloxy group with a substituted or unsubstituted alkyl moiety of $C_2$-$C_8$, and (2)

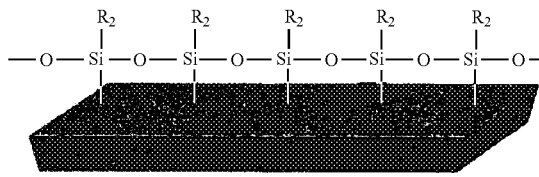

wherein $R_2$ is an alkyl group of $C_1$-$C_{10}$ with an end functional group selected from thiol, amine, epoxy, isocyan, and isothiocyan.

2. The cucurbituril derivative-bonded solid substrate of claim 1, wherein the solid substrate is a glass, a silicon wafer, an indium tin oxide (ITO) glass, an aluminum oxide substrate, or a titanium dioxide substrate.

3. The cucurbituril derivative-bonded solid substrate of claim 1, which is one selected from substrates represented by Formulae 3 through 6:

(3)

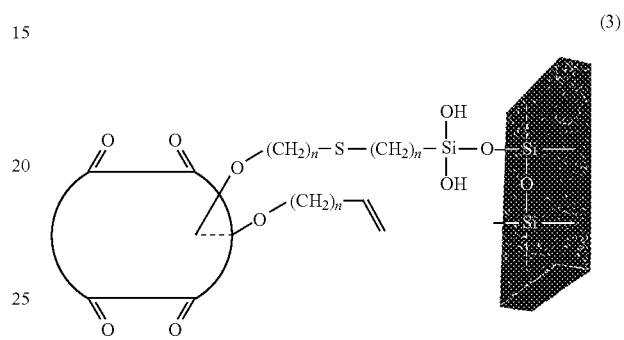

wherein each n is independently an integer of 1 to 20;

(4)

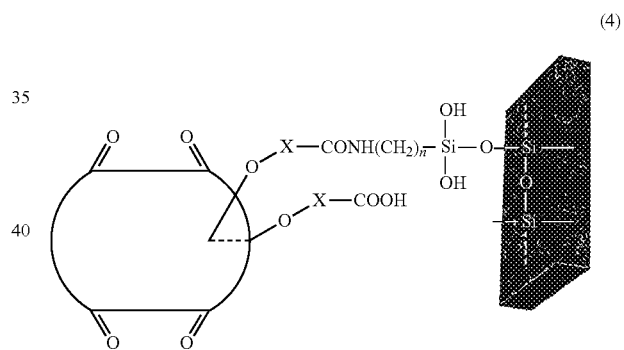

wherein n is an integer of 1 to 20 and X is a dialkylsulfide group with a substituted or unsubstituted alkyl moiety of $C_1$-$C_{20}$ or a substituted or unsubstituted alkyl group of $C_1$-$C_{20}$;

(5)

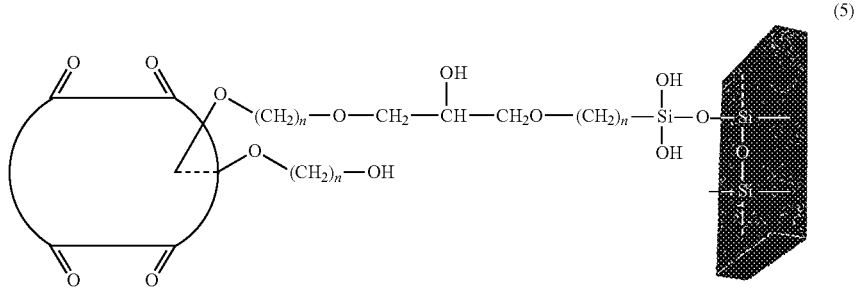

wherein n is an integer of 1 to 20; and

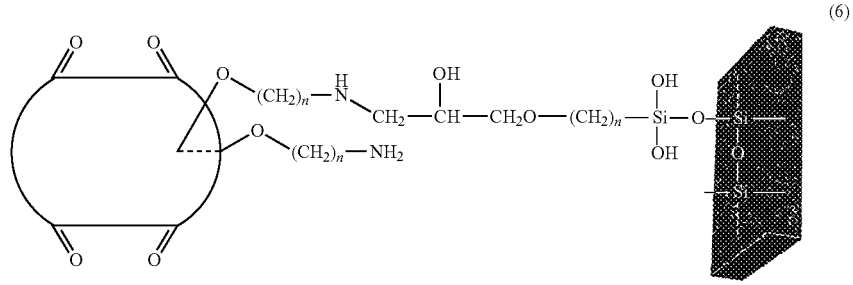
wherein n is an integer of 1 to 20.
4. A protein chip comprising the cucurbituril derivative-bonded solid substrate of claim 1.
5. A gene chip comprising the cucurbituril derivative-bonded solid substrate of claim 1.
6. A sensor for biomaterial assay comprising the cucurbituril derivative-bonded solid substrate of claim 1.
* * * * *